(12) United States Patent
Tybinkowski et al.

(10) Patent No.: US 6,188,743 B1
(45) Date of Patent: Feb. 13, 2001

(54) COMPUTED TOMOGRAPHY SCANNER DRIVE SYSTEM AND BEARING

(75) Inventors: Andrew P. Tybinkowski, Boxford; Michael J. Duffy, Methuen; Lidia Nemirovsky, Salem, all of MA (US)

(73) Assignee: Analogic Corporation, Peabody, MA (US)

( * ) Notice: Under 35 U.S.C. 154(b), the term of this patent shall be extended for 0 days.

(21) Appl. No.: 09/361,452

(22) Filed: Jul. 26, 1999

Related U.S. Application Data

(63) Continuation-in-part of application No. 08/948,930, filed on Oct. 10, 1997, now Pat. No. 5,982,844.

(51) Int. Cl.⁷ .................................................. G01N 23/00
(52) U.S. Cl. .................................................................. 378/4
(58) Field of Search ........................................................ 378/4

(56) References Cited

U.S. PATENT DOCUMENTS

| 4,093,863 | 6/1978 | Zacher, Jr. ........................ 250/445 |
| 4,200,799 | 4/1980 | Saito ................................ 250/445 |
| 4,797,008 | 1/1989 | Helbig et al. ...................... 384/49 |
| 5,071,264 | 12/1991 | Franke et al. ..................... 384/501 |
| 5,448,608 | 9/1995 | Swain et al. ........................ 374/4 |

*Primary Examiner*—Craig E. Church
(74) *Attorney, Agent, or Firm*—McDermott, Will & Emery

(57) ABSTRACT

In an improved computed tomography scanner drive system and bearing configuration, a gantry disk (30) is sheaved about its perimeter (65) such that the gantry is operable as a driven pulley rotatable about an object to be scanned. A motor (46) assembles mounted to a stationary frame (33) includes a similar sheaved drive pulley (80). A belt (64) tensioned between the drive pulley (80) of the motor assembly and the driven pulley of the gantry disk (30) transfers rotational motion of the motor to drive the gantry rotationally about the object. In a preferred embodiment, the belt comprises a V-belt or poly-V-belt (64), and the bearing comprises a wire bearing (59) located proximal to the gantry center of mass. In this manner, the present invention provides a simple and effective technique for driving the gantry about the object, providing sufficiently accurate angular positioning in a reliable and cost effective drive system. Various embodiments of an improved bearing system are also disclosed.

15 Claims, 10 Drawing Sheets

COMPUTED TOMOGRAPHY SCANNER DRIVE SYSTEM AND BEARING

RELATED APPLICATIONS

This application is a continuation-in-part of U.S. application Ser. No. 08/948,930 filed on Oct. 10, 1997 now U.S. Pat. No. 5,982,844 in the names of Andrew P. Tybinkowski, Michael J. Duffy and Gilbert W. McKenna, and assigned to the present assignee.

In addition the application is related to the following U.S. applications filed on Oct. 10, 1997 and commonly assigned with the present application, the contents of which are incorporated herein in their entirety by reference:

U.S. application Ser. No. 08/948,937, "Air Calibration Scan for Computed Tomography Scanner with Obstructing Objects," invented by David A. Schafer, et al., U.S. application Ser. No. 08/948,928, "Computed Tomography Scanning Apparatus and Method With Temperature Compensation for Dark Current Offsets," invented by Christopher C. Ruth, et al., U.S. Pat. No. 5,909,477, "Computed Tomography Scanning Target Detection Using Non-Parallel Slices," invented by Christopher C. Ruth, et al., U.S. Pat. No. 5,901,198, "Computed Tomography Scanning Target Detection Using Target Surface Normals," invented by Christopher C. Ruth, et al., U.S. Pat. No. 5,887,047, "Parallel Processing Architecture for Computed Tomography Scanning System Using Non-Parallel Slices," invented by Christopher C. Ruth, et al., U.S. Pat. No. 5,881,122, "Computed Tomography Scanning Apparatus and Method Generating Parallel Projections Using Non-Parallel Slices," invented by Christopher C. Ruth, et al., U.S. application Ser. No. 08/949,127, "Computed Tomography Scanning Apparatus and Method Using Adaptive Reconstruction Window," invented by Bernard M. Gordon, et al., U.S. application Ser. No. 08/948,450, "Area Detector Array for Computed Tomography Scanning System," invented by David A. Schafer, et al., U.S. application Ser. No. 08/948,692, "Closed Loop Air Conditioning System for a Computed Tomography Scanner," invented by Eric Bailey, et al., U.S. application Ser. No. 08/948,493, "Measurement and Control System for Controlling System Functions as a Function of Rotational Parameters of a Rotating Device," invented by Geoffrey A. Legg, et al., U.S. application Ser. No. 08/948,698, "Rotary Energy Shield for Computed Tomography Scanner," invented by Andrew P. Tybinkowski, et al.,

BACKGROUND OF THE INVENTION

In modern third generation computed tomography (CT) scanners, an X-ray source and detector array are secured on opposite sides of the central opening of an annular disk. The disk is mounted to a gantry support for rotation about a subject or object (positioned in the opening) to be scanned. During a scan, the source and detectors image the object disposed within the machine at incremental scan angles. In fourth generation CT scanners the detectors are fixed relative to the object or subject being scanned, and only the source is mounted on the rotating disk for rotation about the subject or object. In both types of systems a process referred to as reconstruction generates a series of two-dimensional images or slices of the object from the captured data.

For "fixed z-axis" scans (the "z-axis" being the axis of rotation of the disk), the disk and its components rotate about a stationary object or subject with the disk fixed at a specific Z-axis location. For "helical" scans, translational movement along the Z-axis is simultaneous provided between the object or subject and the rotating disk. In both fixed and translational scanning systems, precision in the angular velocity, or rotation rate, of the gantry disk is essential for minimization of reconstruction errors.

Timing belts, or cog belts, have been employed in the past to effect a high degree of precision in rotation rate. A standard timing belt is driven by a motor mounted to the stationary frame. Periodic lateral grooves transverse to the major axis of the belt mesh with teeth on a drive sprocket at the motor and a large driven sprocket mounted to the gantry disk. The driven sprocket must be large enough to avoid interference with the central aperture of the gantry and thus allow room for a object to pass therethrough. For this reason, extraordinarily-large timing belts are required in these systems.

A typical prior art scanner requires at least a six meter timing belt. Timing belts of such a large magnitude are very expensive, as they are difficult to manufacture and often must be custom built, and/or purchased in large quantities. Furthermore, the large driven sprockets are specialized and are therefore expensive, available at a cost of $4,000 to $6,000, depending on the diameter. Alignment between the drive sprocket and driven sprocket must be accurate to a high degree of precision, to avoid lateral walking of the belt relative to the sprockets. Timing belts tend to wear rapidly, and therefore must be replaced frequently, for example once per year for a medical scanner. Replacement is an involved procedure, requiring removal of the scanner system from operation for an extended period of time; perhaps a couple of days. This is due to the fact that in prior art configurations, the driven sprocket is positioned between the annular gantry and the fixed frame. Access to the timing belt for its removal and replacement therefore requires complete removal of the gantry from the frame. Positioning of the sprocket on the component side of the gantry is impractical, since the timing belt would interfere with the rotating gantry components.

A further disadvantage of timing belts in CT systems is their tendency to modulate the rotational speed of the gantry at the frequency of their teeth or cogs. The modulation causes artifacts in the resulting images which must be resolved or otherwise corrected by the image processing system.

In addition, mounting the disk for rotational movement requires some type of reliable support so that the disk reliably rotates with little or no lateral movement in the plane of rotation. In the typical prior art system, standard bearing arrangements, with highly machined races and balls, are expensive. Because of the weight and size of the disk the bearings tend to wear, and are difficult to replace. One solution to this problem has been to mount the disk for centerless rotation on rollers such as shown in U.S. Pat. No. 5,473,657 issued Dec. 5, 1995 in the name of Gilbert W. McKenna, and assigned to the present assignee.

SUMMARY OF THE INVENTION

The present invention is directed to a CT scanner drive assembly that mitigates and/or eliminates the shortcomings associated with prior art scanner drive assemblies described above. The apparatus of the invention comprises an annulus, preferably in the form of a disk, which is sheaved about its perimeter such that the annulus is operable as a driven pulley rotatable about an object to be scanned. Electronic components are preferably mounted to the annulus for performing a tomographic scan of the object. A motor includes a similarly sheaved drive pulley. A belt tensioned between the drive pulley of the motor and the driven pulley of the annulus transfers rotational motion of the motor to the annulus for driving the annulus rotationally about the object during a scan.

In a preferred embodiment, the belt comprises a V-belt or poly-V-belt. An adjustable tensioner draws the motor drive pulley toward or away from the annulus for adjusting the tension of the belt. The annulus preferably comprises a disk having first and second faces. By spacing the disk from the frame, components may be mounted on both faces of the disk, or through apertures in the disk, mitigating space limitations for mounting components to the disk, and balancing the disk center of mass near the disk plane.

In one preferred embodiment, a disk bearing is preferably located at or near the disk center of mass, and mounted to spacers rigidly coupled to the system frame. This configuration reduces the moment arm between the bearing and disk center of mass, improving the life of the bearing and allowing for use of less expensive, simpler bearings, for example Franke four-wire bearings of the type described in U.S. Pat. No. 5,071,264, incorporated herein by reference.

In another preferred embodiment, the annulus is mounted for rotation within the gantry frame wherein opposing grooves are formed in the periphery of the annulus and the inner periphery of the opening of the gantry frame, and are shaped to receive less expensive, simpler bearings, for example Franke four-wire bearings of the type described in U.S. Pat. No. 5,071,264. In one preferred embodiment, the bearing system includes a single set of wire races and spherical bearings disposed therebetween. The spherical bearings are all centered in the center plane of the disk. In another preferred embodiment, the bearing system includes a pair of sets of wire races and spherical bearings disposed therebetween. The spherical bearings of the two sets are respectively disposed in parallel planes, preferably on opposite sides of and equally spaced from the center plane of the disk.

In this manner, the present invention provides a simple and effective technique for driving the annulus about the object or subject to be scanned. The V-belts provide accurate timing—as they minimize slippage, and maximize efficient energy transfer. Further, V-belts offer the additional benefit of a long life time, on the order of five years, before replacement is necessary. Large V-belts are currently available commercially at a relatively low cost of approximately $100.

This configuration is well adapted for continuous operation in an airport setting for baggage scanning applications and systems of the type that use CT scanners and which run continuously for 18–20 hours daily. By conveniently locating the belt on an outer edge of the annulus or disk, maintenance of the belt is relatively straightforward and can be performed expeditiously, on the order of 1–2 hours, without the need for disassembling the entire gantry as in the prior art. In addition, V-belts are generally relatively flexible and can be mounted without the need for critical alignment tolerances of prior art timing belts. The flexibility of the V-belt, in combination with its longitudinal grooves provide a smooth interface for driving the disk in continuous motion, without modulating the rotational speed. The drive system therefore makes no contribution to image artifacts.

In addition, the use of the simpler bearings allows for easier servicing of the scanner.

BRIEF DESCRIPTION OF THE DRAWINGS

The foregoing and other objects, features and advantages of the invention will be apparent from the more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENTS

Figure 1:
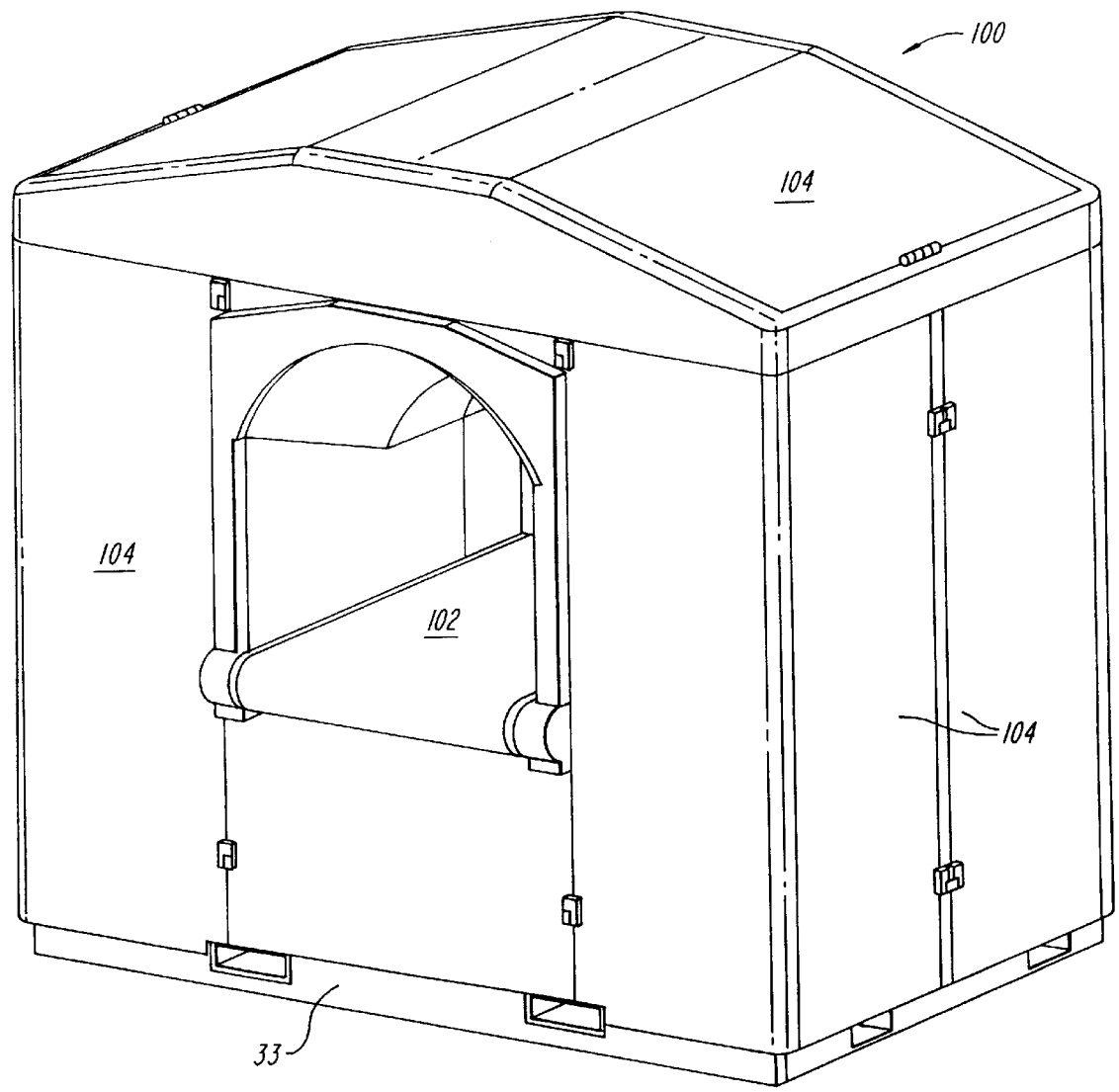
FIG. 1 is a perspective view of an outer console of a baggage scanner system of the type using a CT scanner constructed in accordance with the present invention.

FIG. 1 is a perspective illustration of outer console 100 of a baggage scanning system of the type using an X-ray computed tomography (CT) scanner. The console 100 comprises a plurality of panels 104 mounted to a rigid frame (see FIGS. 2 and 3) erected on a base 33. The panels 104 are hinged to the frame or are otherwise removable to provide access to the inner components of the scanner. A conveyor 102 transports objects to be scanned, for example, airport baggage, into the scanning area. As is well known, where the CT scanner is employed as a medical scanner, a suitable patient table usually supports a patient within the CT scanner so that a select portion of the patient can be scanned.

Figure 2:
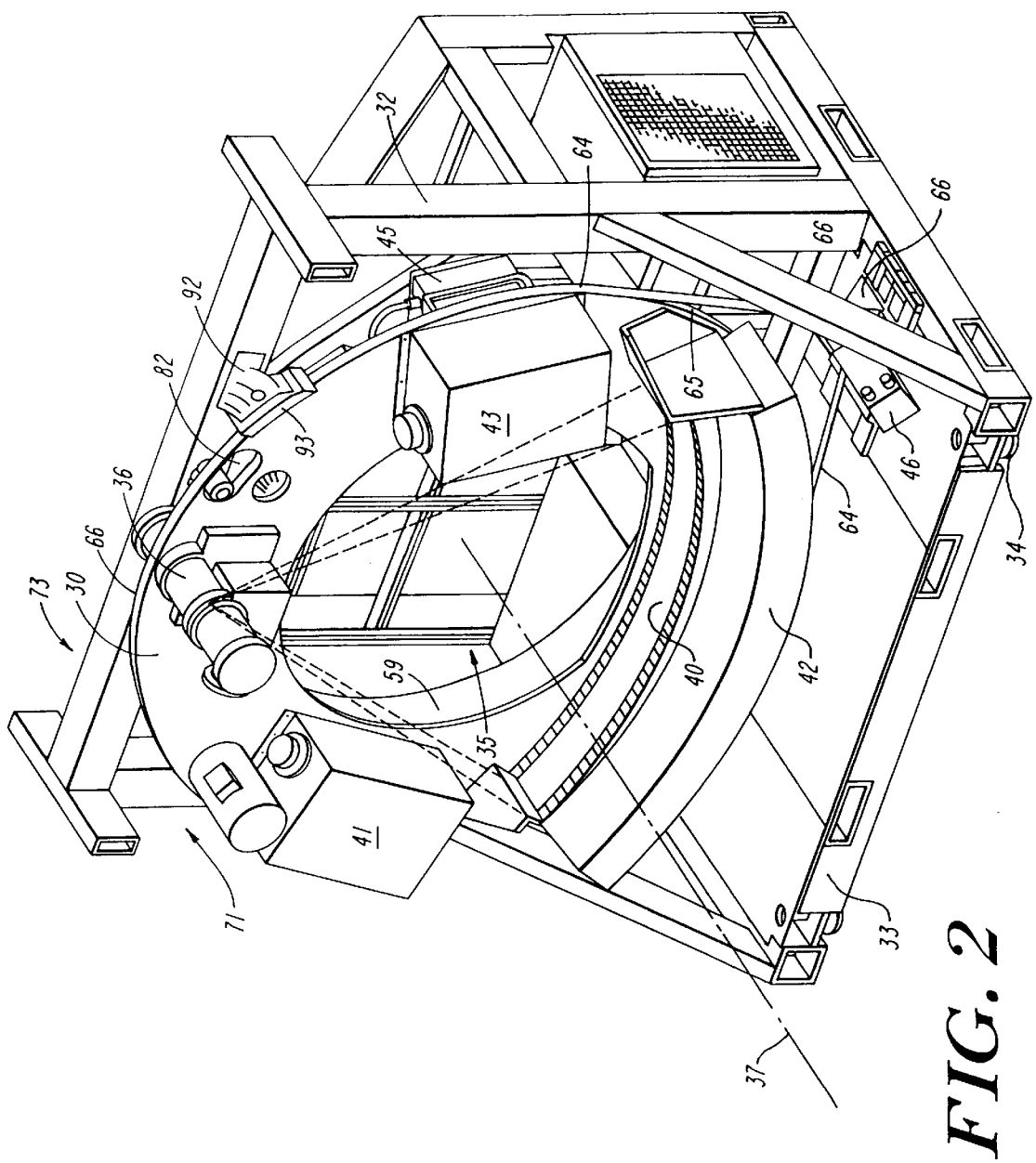
FIG. 2 is a front perspective view of a scanner frame and gantry disk configuration in accordance with the present invention.

FIG. 2 is a front perspective view of the primary components of a CT scanner in accordance with the present invention. A rigid vertical frame 32 is erected on a base 33. The base 33 includes a plurality of height-adjustable feet 34 for leveling the system.

An annulus or disk 30 preferably formed of a lightweight, rigid material such as aluminum, magnesium-aluminum alloy or the like is rotatably mounted on the frame 32. The annulus 30 may be solid or hollow, preferably substantially uniform in cross-section and mass throughout, and is generally radially symmetrical, preferably in the shape of a disk or drum. To ensure that the grain or crystal structure of the disk is structurally uniform, it is preferred that the disk be formed by a precision casting as a single unit, annealed and finished by machining.

An X-ray source tube or source 36 is positioned on the disk 30 for directing an X-ray beam along the plane of the disk 30 across aperture 35 substantially perpendicular to the axis of rotation 37. Similarly, an X-ray detector array 40 is mounted on the disk 30 opposite the source 36 for detecting emitted X-rays 38. Additional components, for example, a data acquisition system 42 for the detector array 40, X-ray power supply cathode 41 and anode 43, air conditioning or cooling systems 45 and related electronics are likewise mounted on both front and rear faces 71, 73 of the gantry disk 30. The disk 30 is rotatably mounted to the vertical frame 32 at bearing 59, the details of which are described below.

A motor 46 and an associated drive pulley 80 (see FIGS. 6A and 6B) coupled thereto drive a belt 64. The belt 64 in turn is coupled to the outer perimeter of the gantry disk 30 for rotating the disk which operates as a driven pulley. The belt 64 preferably comprises a V-belt, for example a poly-V-belt, to confer various advantages described throughout the specification, including low cost, increased longevity, and reduced sensitivity to alignment. Such belts are commercially available from various vendors, for example Browning Inc., Gates Inc., Goodyear Inc., and Jason Inc.

The outer edge 65 of the disk 30 is sheaved to interface with the longitudinal grooves of the poly-V-belt 64. The cross-sectional V-shaped geometry of the belt in combination with the large disk circumference serve to minimize belt slippage, maximizing accuracy in rotational disk positioning and rotation rate. Tension in the belt 64 is controlled by tensioner 66 which adjusts the distance between the motor drive pulley 80 (see FIG. 6) and driven disk 30. Replacement of the belt in this configuration simply involves loosening of the belt 64 at tensioner 66 and removal and replacement of the belt 64 at the front face 71 of the disk. Removal of the disk 30 from frame 32 is unnecessary for belt service in the present configuration, and therefore the belt can be removed and replaced in a matter of minutes.

Figure 6A:
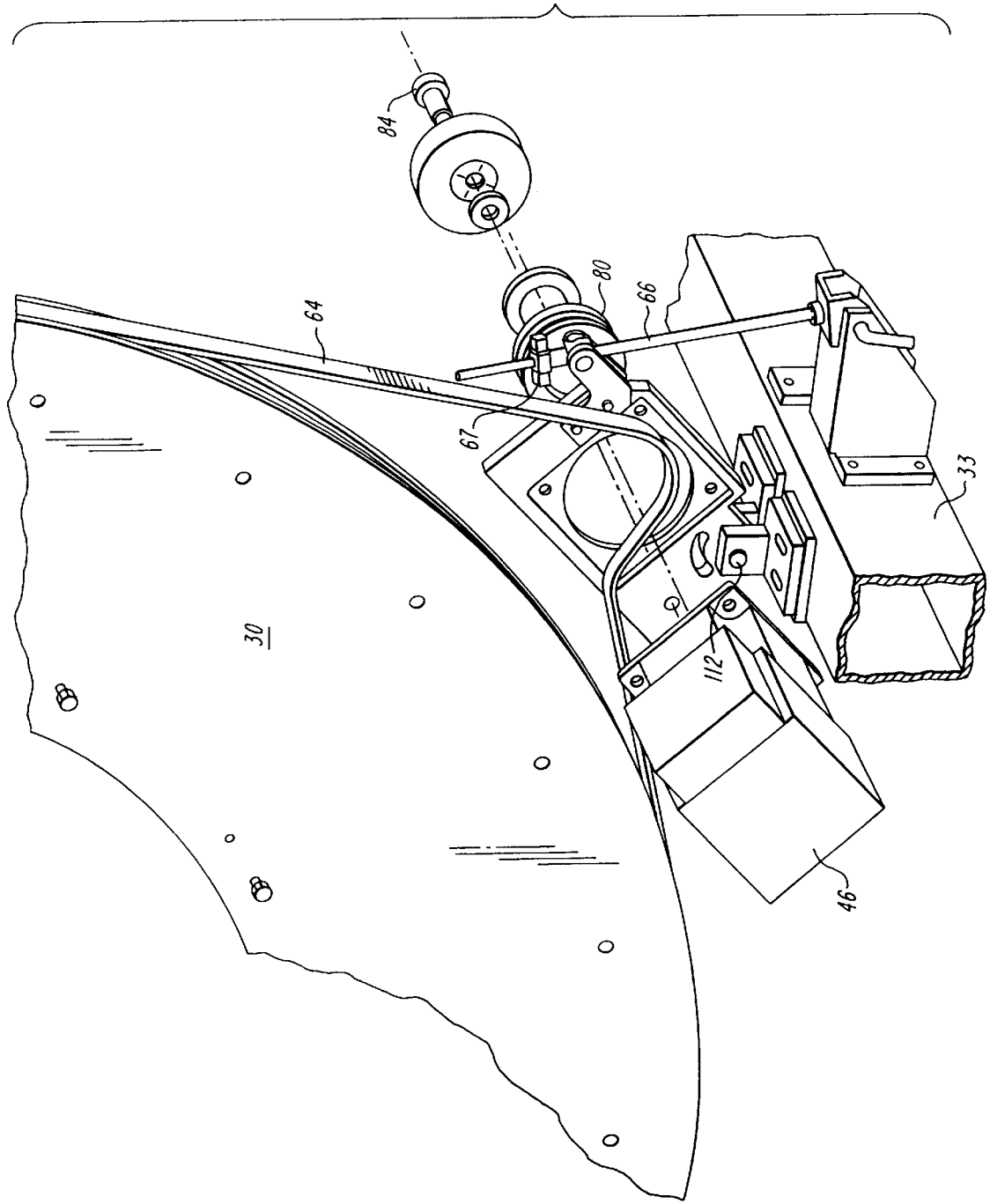
FIGS. 6A and 6B are exploded perspective views of alternative embodiments of the motor and drive pulley tensioner apparatus in accordance with the present invention.

FIG. 6A is an exploded perspective view of a motor and drive pulley system and corresponding belt tensioner in accordance with the present invention. The motor 46 is coupled to the base 33 at pivot 112. A taper bushing 84 mounts a drive sheave to the motor axle. A tensioner 66 mounted to the motor plate and adjustable by nut 67 adjusts the distance between the drive pulley 80 and the gantry disk 30, thereby adjusting the tension of the belt 64. The rod or tensioner 66 is threaded such that tightening of the nut 67 relative to the rod causes the motor 46 to pivot away from the gantry disk 30 thereby tensioning the belt 64. For removing the belt 64 during servicing, the nut 67 is loosened, removing tension in the belt which can thereafter easily be removed at the front face of the gantry disk 30.

Figure 6B:
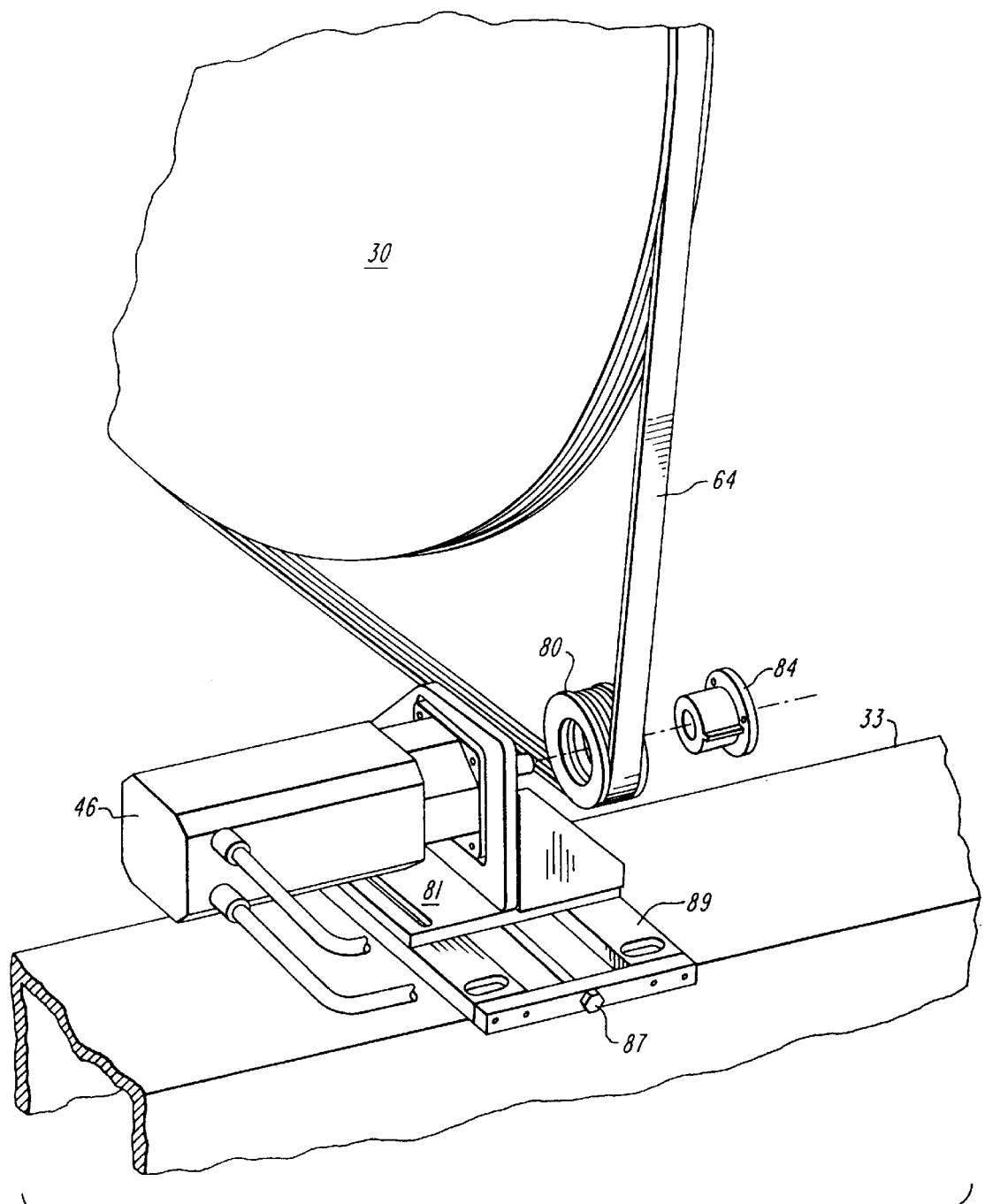

FIG. 6B is a perspective view of an alternative belt tensioner configuration. In this embodiment, the motor 46 is mounted to a movable plate 81 which slides relative to a fixed plate 89. A tension bolt 87 is adjustable for moving the motor 46 relative to the gantry disk 30, thereby tensioning the belt 64.

Figure 3:
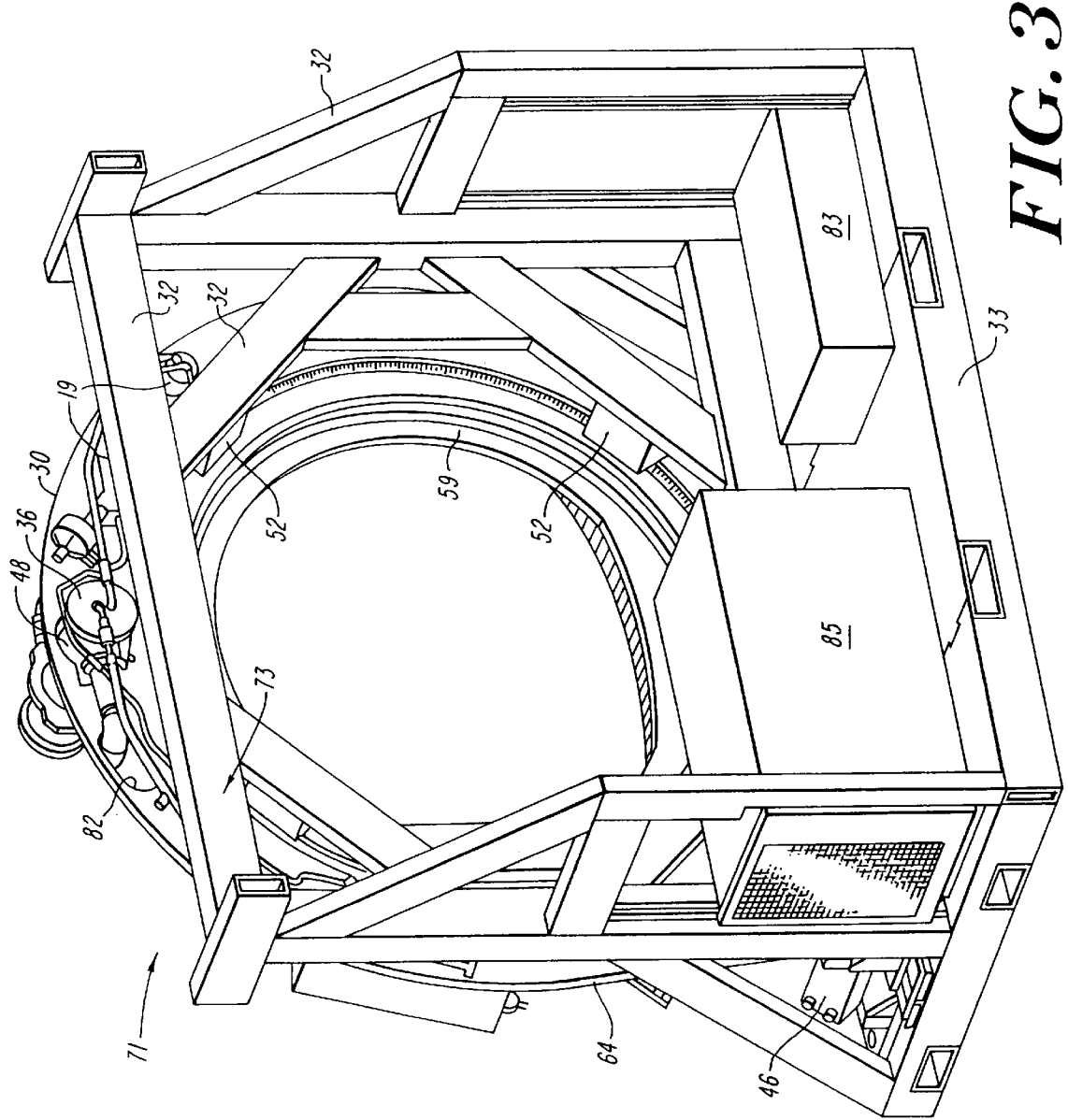
FIG. 3 is a rear perspective view of the frame and gantry disk configuration of FIG. 2 in accordance with the present invention.

FIG. 3 is a rear perspective view of the gantry disk 30 and frame 32. Gantry components mounted on the rear face 73 of the gantry disk 30 are visible in this view, for example, the rear portion of X-ray source 36, and associated cooling systems 19, along with power distribution assemblies, communication units, oil pumps, etc., hidden from view. To provide room for rotation of the rear-face components between the gantry disk 30 and the frame 32, bearing 59 is distanced from the vertical frame by frame spacers or extenders 52. Apertures 82 are provided in the gantry disk 30 to allow for mounting of components through the disk; for example X-ray source 36 passes through aperture 48 and extends from both disk faces 71, 73. Additional apertures 82 allow for passage of signals, power cables, and cooling fluids between components on opposite faces of the gantry disk 30.

Slip rings and corresponding brushes (not shown) transmit power signals and high-bandwidth data signals between components of the gantry disk 30 and frame 32. Microwave transmitter/receiver pairs provide further communication of low-bandwidth control signals. The signals are transmitted to a processing unit 83 which converts the signals to images. Air conditioner system 45 provides for circulation of air and maintains system temperature.

Figure 4:
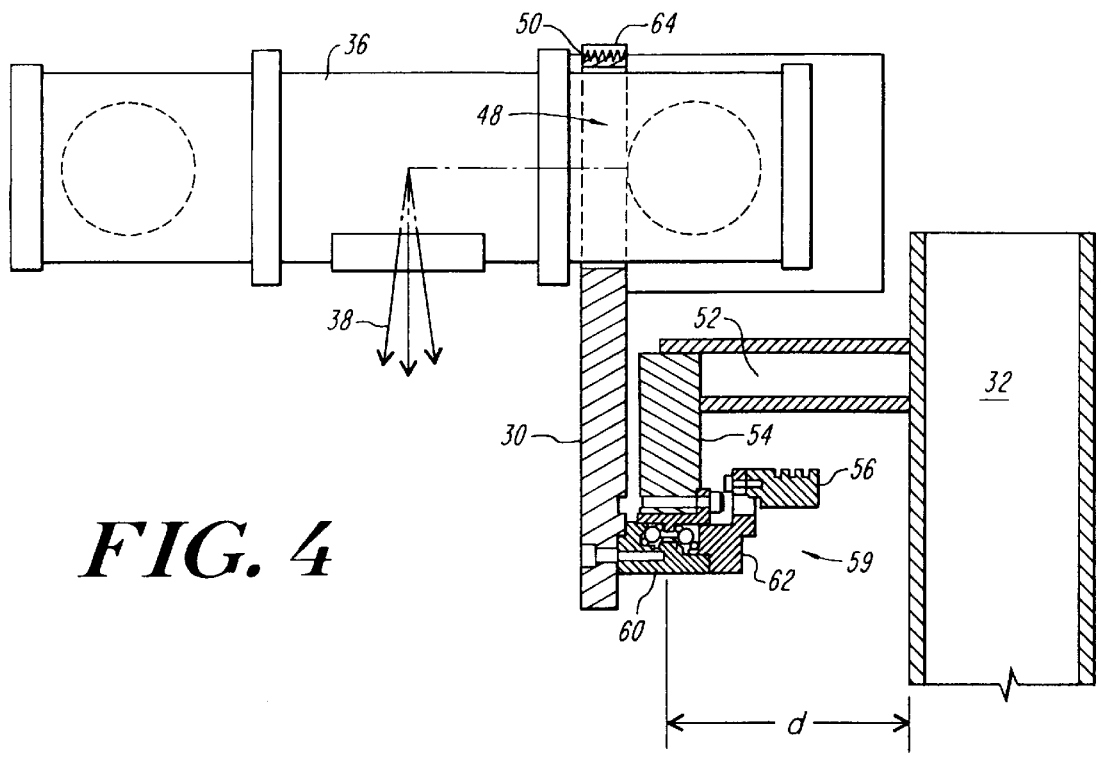
FIG. 4 is a side cross-sectional view of a portion of the gantry and frame of FIGS. 2 and 3, illustrating the sheaved outer edge of the gantry disk and a preferred bearing configuration in accordance with the present invention.

FIG. 4 is a sectional side view of the relationship of the gantry disk 30, bearing 59, and vertical frame 32. The vertical frame 32 supports the gantry 30 system in an upright position, substantially perpendicular to the floor. Frame spacers, or extenders 52 relocate the position of the gantry bearing 59 a distance d from the frame 32 such that the various gantry components are mountable on the rear face of the gantry disk 30 without interfering with the vertical frame 32 during disk rotation. Ring frame 54 serves as a mount for the bearing 59.

Figure 7:
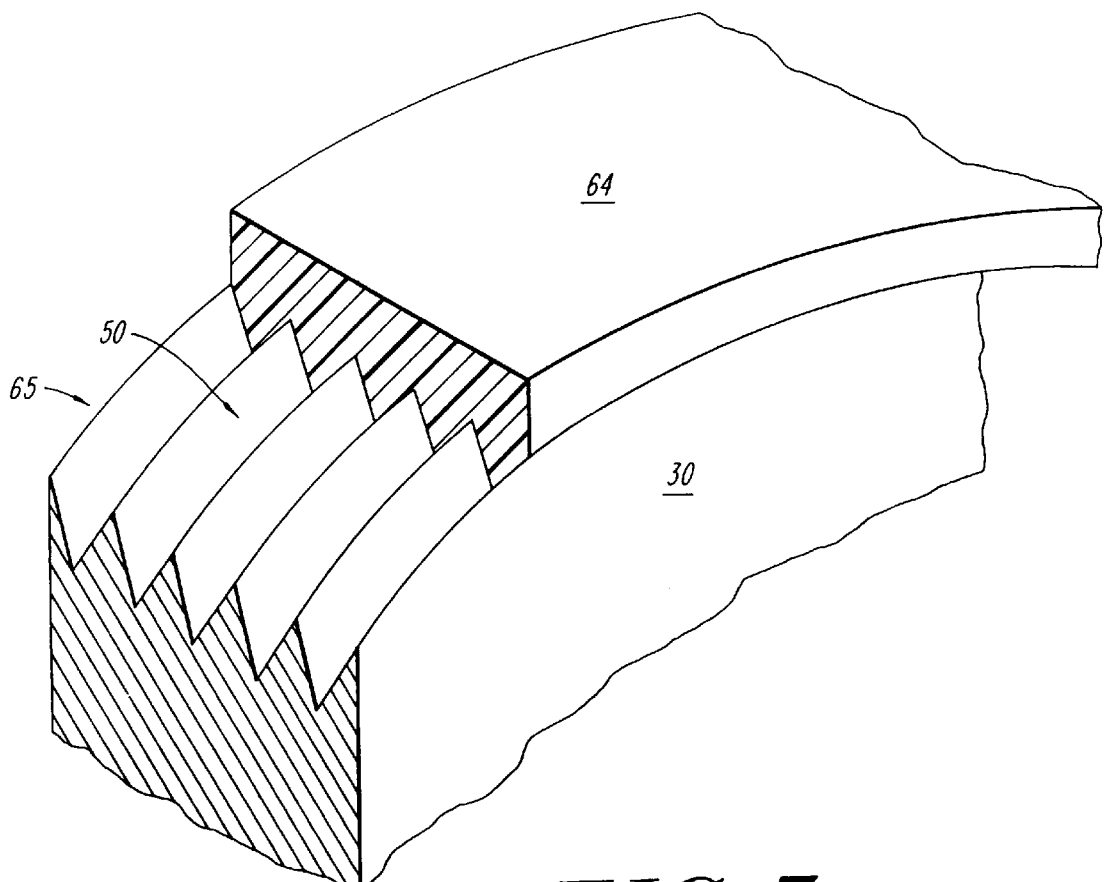
FIG. 7 is a close-up perspective view of the interface between the V-belt and the sheaved outer perimeter of the gantry disk in accordance with the present invention.

The interface between the longitudinal sheaves 50 on the outer perimeter of the gantry disk 30 and the mating longitudinal grooves on the poly-V-belt 64 is visible in the side view of FIG. 4. A close-up perspective view of this interface is shown in FIG. 7. The poly-V-belt and sheave configuration serves to increase the surface area of the interface, thereby minimizing belt slippage.

Although the respective positions of the spacers 52 and bearing 59 could be reversed, with the spacers 52 mounted on the gantry disk 30 surface, and the bearing 59 mounted to the vertical frame 32, such a configuration would increase the moment arm between the bearing and the center of mass of the disk, thereby increasing the radial load and trust load on the bearing. This would require a more robust and therefore more expensive bearing unit. By locating the bearing 59 near or at the center of mass of the gantry, the present invention allows for use of an inexpensive bearing configuration. This, in combination with the mounting of components on both sides of the gantry disk 30, achieves dynamic balancing of the disk relative to the bearing, and reduces the cantilevered load on the bearing.

Figure 5:
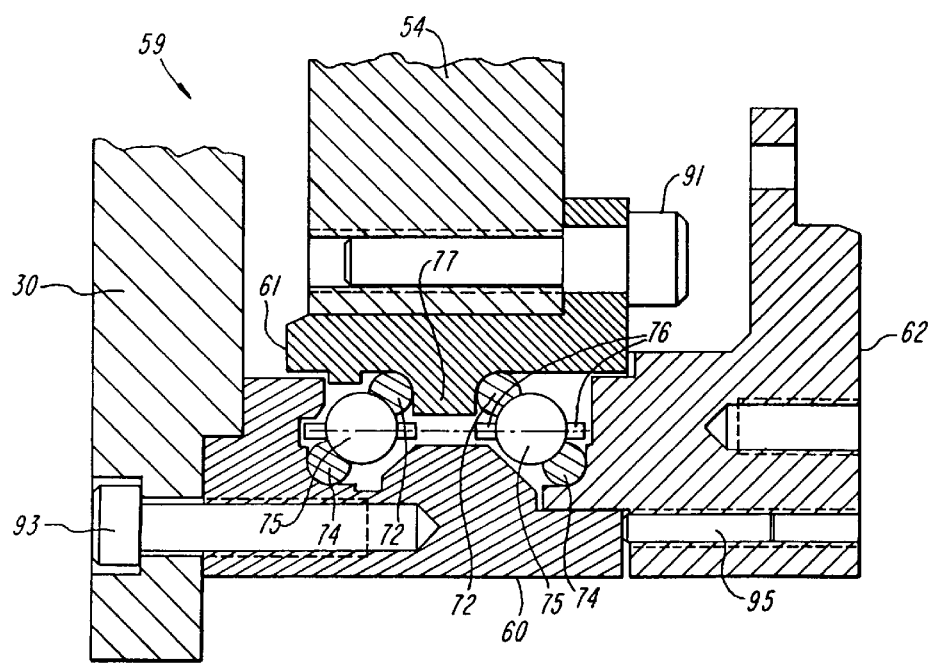
FIG. 5 is a close-up cut-away side view of one preferred embodiment of the improved bearing configuration of the present invention.

FIG. 5 is a close-up sectional view of the interface of bearing 59, which is preferably configured to emulate the well-known Franke bearing interface, as disclosed in U.S. Pat. Nos. 4,797,008 and 5,071,264, incorporated herein by reference. A fixed outer bearing housing 61 mounts to the ring frame 54 by bolts 91. Outer bearing wires 72 are deposited on each inside corner of bearing lip 77, which serves to separate the bearing runs. An inner bearing housing, including first and second inner rings 60, 62 respectively, mounts to the gantry disk 30 by bolts 93. The inner housing includes inner bearing wires 74 laid along the outer corners of the inner bearing housing as illustrated. Suspended between the outer and inner wire races of bearing wires 72, 74 are spherical ball bearings 75, which glide across the wires with minimal resistance as the gantry disk 30 rotates. Side separators or ball spacers 76 prevent adjacent balls from contacting or otherwise interfering with each other. Preloading of the bearings is controlled by preload bolts 95.

The bearing configuration of the present invention confers several advantages. The bearing/wire interface operates with less friction than traditional bearing races as the wires provide a smooth and efficient track for the bearings. No custom bearing housing is required, as the housing is provided by the inner surfaces of the races. The present bearing configuration requires 10 ft-lbs. of turning torque as opposed to the less efficient prior art designs requiring 50 ft-lbs. of turning torque, assuming a gantry disk of 6 feet in diameter, weighing 1500 lbs, allowing use of a smaller motor, for example a 0.5 horsepower, for rotating the gantry. Furthermore, this bearing configuration is light weight, operates quietly, and is relatively inexpensive.

Figure 8B:
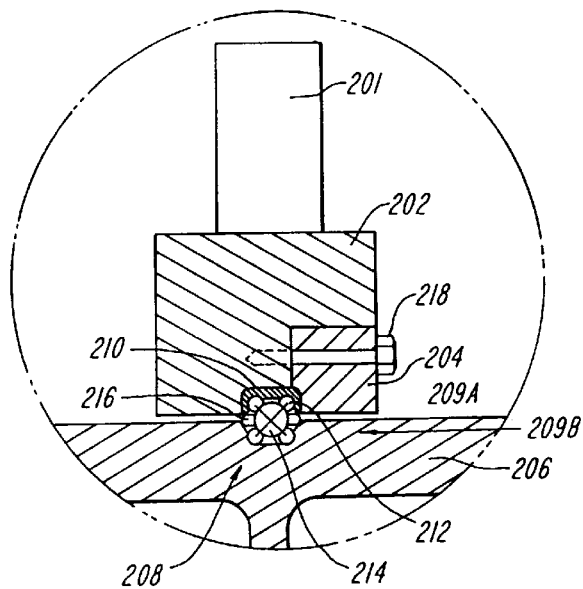
FIG. 8B is a close-up cut-away view of the improved bearing configuration of FIG. 8A.
Figure 8A:
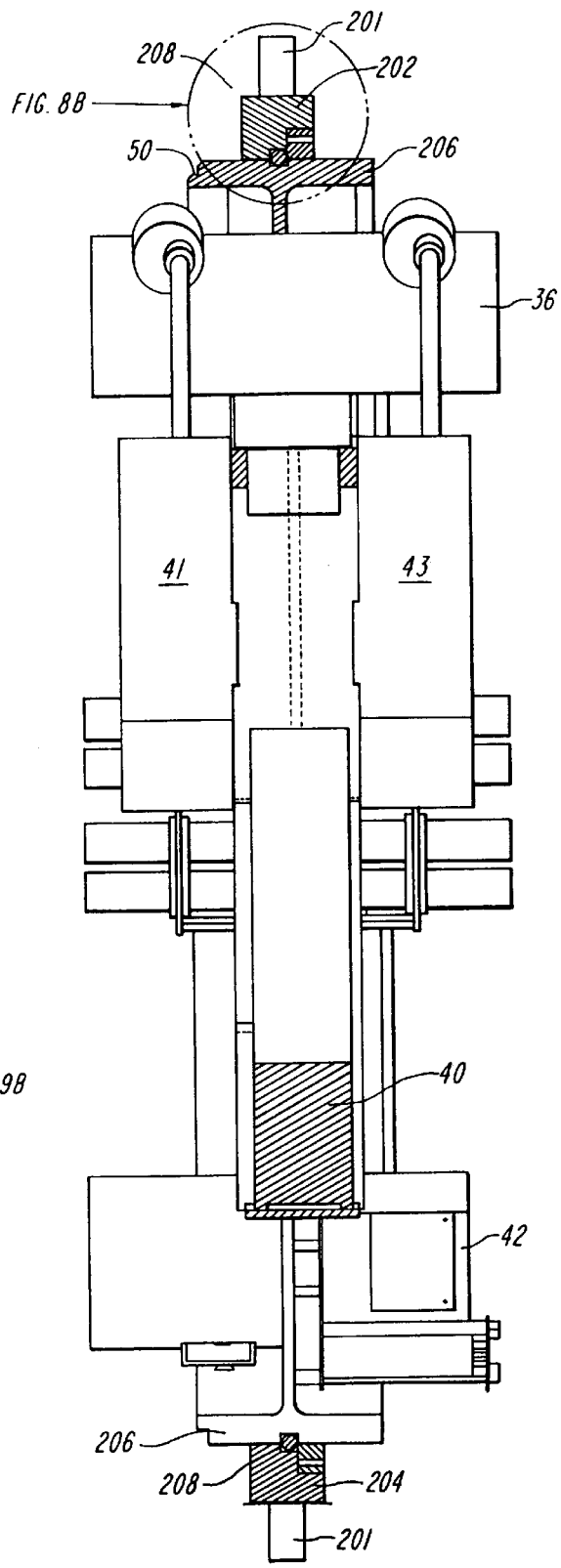
FIG. 8A is a side cross-sectional view of a portion of the annulus and gantry frame of another preferred embodiment of the improved bearing configuration of the present invention.

An alternative bearing configuration is depicted in FIG. 8A, with a close-up cutaway side view of the bearing arrangement given in FIG. 8B. In this configuration, the annulus, or disk 206, is mounted for rotation within a circular gantry frame ring 202, in turn mounted to a pivot shaft 201. The pivot shaft 201 allows for pivoting of the entire frame at an angle relative to the translation axis through the center of the disk. The stationary mounting frame ring 202 is provided with a groove 209A opposite a similar groove 209B on the periphery of the rotatable annulus 206. The opposed grooves 209A, 209B are shaped to receive bearings 209, comprising wire races 212 and balls 214, for example, the Franke bearings of the type described above. A pre-load ring 204 secured by bolts 218 secures the bearing 208 in place and urges the wire races 212 against the balls 214. Cages 216 space the balls 214 relative to one another, as described above. An elastomer ring 210 may be mounted in either or both grooves to house the bearings and provide for more quiet operation during rotation of the disk 206. A sheave 50 is preferably provided on the outer perimeter of the disk 206 for receiving a V-belt, conferring the advantages described above.

Figure 9A:
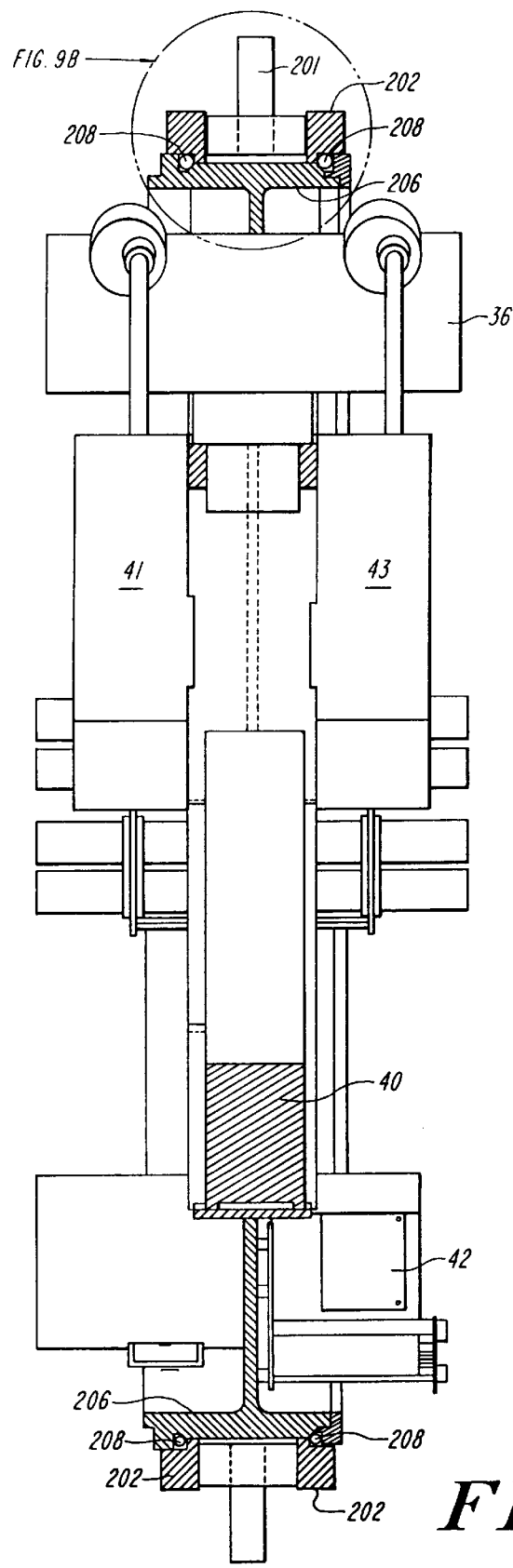
FIG. 9A is a side cross-sectional view of a portion of the annulus and gantry frame of a third preferred embodiment of the improved bearing configuration of the present invention.
Figure 9B:
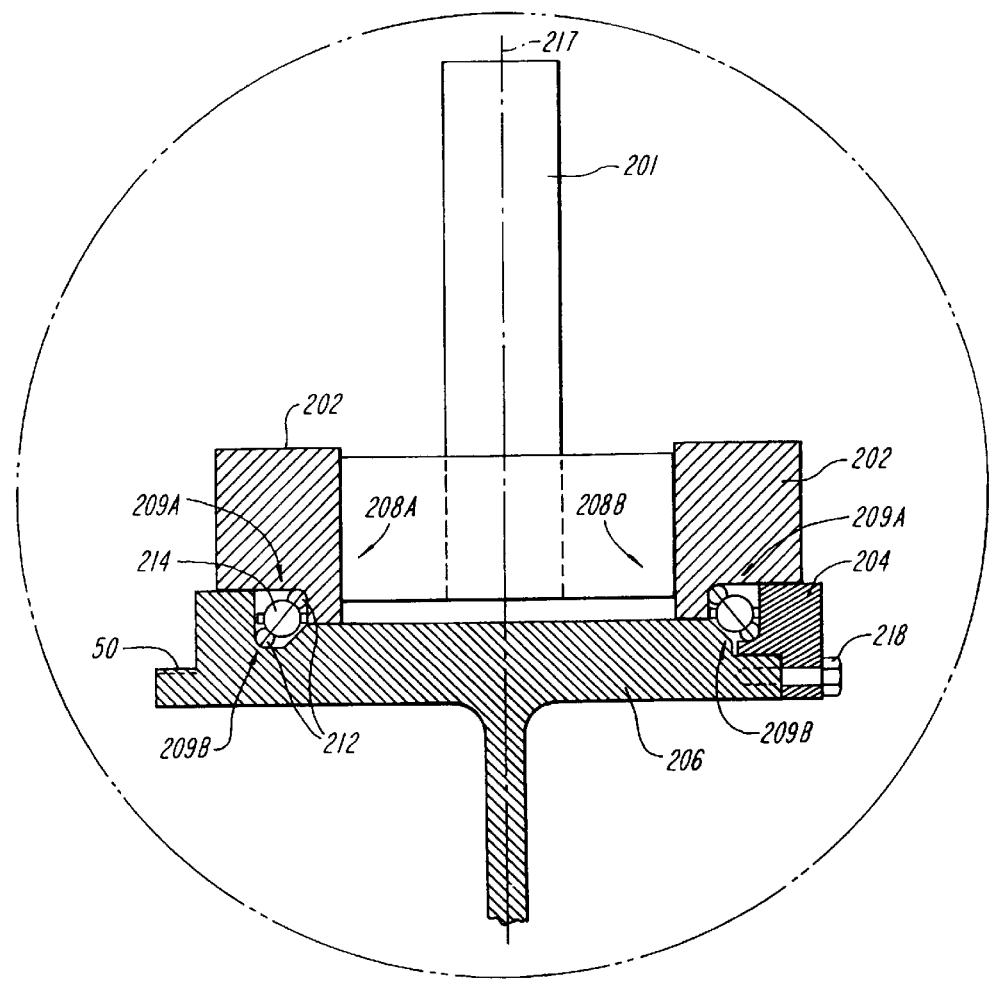
FIG. 9B is a close-up cut-away view of the improved bearing configuration of FIG. 9A.

FIG. 9A and FIG. 9B are a side view and a close-up cutaway view respectively of an alternative bearing configuration in accordance with the present invention. In this configuration, first and second pairs of opposed grooves 209A, 209B are formed on the stationary mounting frame 202 and the rotatable annulus 206 respectively. First and second bearings 208A, 208B are positioned in the grooves 209 to provide an interface between the frame and rotatable annulus. In this configuration, each bearing comprises first and second wire races 212, between which balls 214 communicate. By spacing apart the bearings 208A, 208B on opposite sides of the center axis 217 this configuration provides for a more stable structure and therefore allows for reliable operation at increased rotation speeds.

Figure 10:
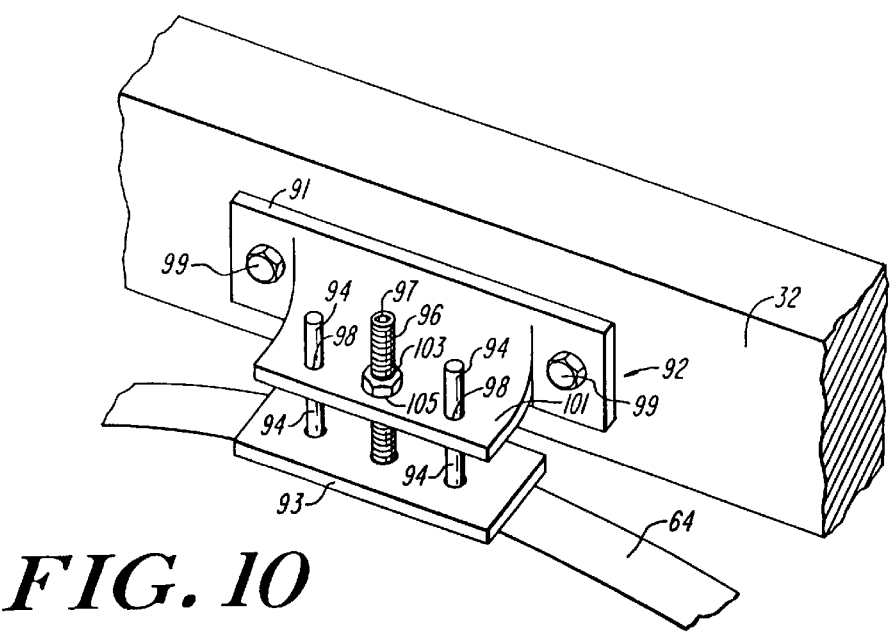
FIG. 10 is a perspective view of a disk lock in accordance with the present invention.

The present invention may optionally further include a disk lock 92 (see FIG. 2) mounted to the rigid frame 32 for preventing rotation of the disk 30, for example, during component installation or maintenance, or during shipping. In a preferred embodiment, a lock pad 93 is activated by engagement means and is urged against the drive belt 64. As shown in the perspective close-up view of FIG. 10, the disk lock 92 includes a mount 91 fixed to the frame 32 by bolts 99. A lock pad 93 is suspended below an extension 101 of the mount 91, and is rotatably secured to a threaded adjustment bolt 96 interfacing with threaded hole 105 on the extension 101. As the pad 93 position is adjusted via Allen wrench aperture 97, guides 94 fixedly mounted to the lock pad 93 slide relative to holes 98 in the mount extension 101. Once in position, a lock nut 103 secures the disk lock, preventing vertical movement. The lock pad 93 is preferably adapted to interface with the outer edge of the V-belt 64 as shown in FIG. 10.

In an experimental apparatus, the gantry disk comprised a 6 ft. diameter aluminum disk weighing 1500 lbs. A commercially available poly-V-belt having 5 grooves, and commercially available at a cost of $150, was sufficient for rotating the gantry at 90 RPM, using a 1.5 horsepower motor, and delivering an angular rate accuracy better than 0.1%, exceeding the angular rate precision required for accurate scanning.

While this invention has been particularly shown and described with references to preferred embodiments thereof, it will be understood by those skilled in the art that various changes in form and details may be made therein without departing from the spirit and scope of the invention as defined by the appended claims. For example, while the embodiment shown in the drawings illustrate a CT Scanner of the third generation type, the invention can be used in CT Scanner of the fourth generation type.

We claim:

1. An X-ray tomography scanning system comprising:
   a rigid frame;
   a disk having a central aperture for receiving an object to be scanned;
   electronics mounted to first and second faces of said disk for performing a tomographic scan of said object; and
   a circular bearing system mounted between said frame and said disk, said bearing system including respective rings of resilient wire serving as races for a plurality of spherical bearings which roll between the races as the disk rotates relative to the frame.

2. The X-ray tomography scanning system of claim 1, wherein said disk further includes component apertures such that electronics can be mounted through said disk.

3. The X-ray tomography scanning system of claim 1, wherein said bearing comprises a four-wire Franke bearing.

4. The X-ray tomography scanning system of claim 1, wherein said disk includes a sheaved outer perimeter such that said disk is operable as a driven pulley.

5. The X-ray tomography scanning system of claim 4, further comprising:
   a motor mounted to said frame, said motor including a sheaved drive pulley; and
   a belt tensioned between said drive pulley and said driven pulley for transferring rotational motion of said motor to said disk for driving said disk in rotational motion about said object.

6. The X-ray tomography scanning system of claim 5, wherein the belt is a poly-V-belt.

7. The X-ray tomography scanning system of claim 1, wherein the bearing system includes first and second bearing housings in opposed rotatable relationship, said first and second opposed bearing housings including respective rings of resilient wire serving as races for a plurality of spherical bearings adapted to roll between the housings on the races as the disk rotates relative to the frame.

8. The X-ray tomography scanning system of claim 1, wherein the disk is mounted so as to be cantilevered with respect to the frame.

9. The X-ray tomography scanning system of claim 1, wherein the disk is rotationally mounted within an opening of the frame, the disk including at least one groove around the outer periphery of the disk for receiving one race of wires of said bearing system, and the frame including at least one groove disposed within the opening of the frame and opposing the groove of the disk for receiving another race of wires of the bearing system, said spherical bearings being disposed between said races.

10. The X-ray tomography scanning system of claim 9, wherein the disk defines a center plane normal the axis of rotation of the disk, and the races of wires are disposed so the spherical bearings are centered in the center plane.

11. The X-ray tomography scanning system of claim 1, wherein the disk is rotationally mounted within an opening of the frame, the disk including at least two grooves around the outer periphery of the disk, each groove for receiving one race of wires of said bearing system, and the frame including at least two grooves around the opening of the frame and respectively opposing the two grooves of the disk for receiving two other races of wires of the bearing system so as to form two sets of opposing races of wires, said spherical bearings being disposed between the races of each set.

12. The X-ray tomography scanning system of claim 11, wherein the races of wires received in opposing grooves are disposed so the spherical bearings of the two sets of opposing races are centered in two parallel planes.

13. The X-ray tomography scanning system of claim 12, wherein the disk defines a center plane normal to the axis of rotation of the disk, nd the two parallel planes are disposed on opposite sides of and spaced an equal distance from the center plane.

14. The X-ray tomograph scanning system of claim 1, further comprising a disk lock mounted to the frame, said disk lock including a pad and engagement means, said engagement means for urging the pad toward the disk for locking the disk in place.

15. The X-ray tomography scanning system of claim 14, wherein the disk is operable as a driven pulley to be driven by a belt, and wherein the pad is urged toward the belt for locking the disk in place.

* * * * *